United States Patent [19]

Gerdt

[11] Patent Number: 5,074,309
[45] Date of Patent: Dec. 24, 1991

[54] DEVICE FOR MONITORING CARDIOVASCULAR SIGNALS AND FIBER OPTIC COUPLER PHONOCARDIO SENSOR THEREFOR

[75] Inventor: David W. Gerdt, Charlottesville, Va.

[73] Assignee: Sperry Marine Inc., Charlottesville, Va.

[21] Appl. No.: 444,920

[22] Filed: Dec. 4, 1989

[51] Int. Cl.⁵ .............................................. A61B 5/02
[52] U.S. Cl. ........................... 128/715; 128/714; 128/687; 128/691; 73/705; 250/227.14; 250/227.24; 250/227.28; 250/231.1
[58] Field of Search ............... 128/701, 715, 717, 691, 128/694, 687, 721; 73/655, 656, 603, 705, 715; 250/227, 231 P, 227.14, 227.28, 227.24, 231.10, 231.19; 350/96.1, 96.15

[56] References Cited

U.S. PATENT DOCUMENTS

| | | | |
|---|---|---|---|
| 4,634,858 | 1/1987 | Gerdt | 73/705 |
| 4,663,185 | 5/1987 | Eckberg | 350/96.1 |
| 4,664,129 | 5/1987 | Helzel et al. | 128/721 |
| 4,672,976 | 6/1987 | Kroll | 128/773 |
| 4,733,931 | 5/1988 | Fan | 350/96.15 |
| 4,752,141 | 6/1988 | Sun et al. | 73/705 |
| 4,795,226 | 1/1989 | Bennion et al. | 350/96.15 |
| 4,805,630 | 3/1989 | Sterey | 73/705 |
| 4,879,454 | 11/1989 | Gerdt | 350/96.1 |
| 4,883,338 | 11/1989 | Abe et al. | 350/96.1 |
| 4,932,262 | 6/1990 | Wlodarczyk | 73/705 |
| 4,947,865 | 8/1990 | Hon et al. | 128/775 |

*Primary Examiner*—Stephen C. Pellegrino
*Assistant Examiner*—Robin R. Longo
*Attorney, Agent, or Firm*—Seymour Levine; Abert B. Cooper

[57] ABSTRACT

Cardiovascular sounds from a patient's body are monitored by placing a fiber optic coupler sensor at an appropriate location on the patient to sense the sounds. The sensor is comprised of all dielectric material having a variable coupler waist region encapsulated in material with index of refraction that varies with applied stress. Stress is induced in the encapsulating material in response to the cardiovascular sounds. Sensor configurations include encapsulating material membranes with curved surfaces to enhance sensitivity.

10 Claims, 4 Drawing Sheets

DEVICE FOR MONITORING CARDIOVASCULAR SIGNALS AND FIBER OPTIC COUPLER PHONOCARDIO SENSOR THEREFOR

BACKGROUND OF THE INVENTION

1. Field of the Invention

The invention relates to detecting the audible sounds and sub-audible sounds (infra-sound) made by the heart, pulse and circulatory system, particularly with respect to non-invasive cardiological sensors. Generally, the invention relates to non-invasive detection of body sounds for the purpose of diagnosis such as by spectral analysis.

2. Description of the Prior Art

Phonocardio sensors of present day design are inadequate and even hazardous for numerous applications. Appropriate sensors are desirable in magnetic resonance imaging (MRI) systems for sensing cardiovascular sounds such as pulse as well as breathing rate and temperature. In MRI systems, gated imaging is desirable in reducing image deterioration resulting from blood and fluid pressure waves related to pulse. Such waves generate tissue motion and blur MRI images which may be time exposed for as long as four minutes. There are not any known phonocardio sensors capable of safely sensing the pulses of all patients.

Electrically based sensors, which have metallic components such as electrical conductors and wires, generally present a shock hazard, and in MRI applications, a burn as well as a shock hazard. In MRI systems, radio frequency currents induced in metallic components presents a shock hazard to the patients monitored by such sensors and radio frequency heating induced in such metallic components presents a burn hazard. Additionally, lightning striking a hospital or even near a hospital can generate large induced currents in wires attached to patients. Less than a milliampere of current can result in cardiac arrest. In addition, such electrical medical sensors utilize very high input impedance amplifiers to mitigate the shock hazard. High input impedance amplifiers are, however, sensitive to picking up electrical noise and interference thereby diminishing the quality of the data provided and reducing the usefulness of such devices.

One form of phonocardio sensor in use today is the electrical microphone. Such phonocardio microphones suffer from the shock and burn hazards described above. Additionally, such microphones suffer from severe one-over-frequency (1/f) or "pink" noise, which propagates through the detectors and amplifiers, generally rendering such devices useless below approximately 25 Hz and requiring that the sensors be utilized in very quiet environments. It is appreciated that MRI systems are acoustically noisy and utilize the intense high frequency magnetic fields which induce the hazardous radio frequency currents and heating. The records generated by such phonocardio microphones are generally of poor quality.

In a small number of advanced centers for MRI research, a crude electrical sensor is utilized which also suffers from the shock and burn hazards described above. This sensor utilizes a light source and a detector to monitor flushing of the skin. When skin is pressed or stretched, cycles of red flushing is detectable at the pulse rate in many patients. Although this flushing affect is barely detectable, under appropriate conditions of illumination, a sensor of this type is operative in approximately 80% of the population. The remaining 20% cannot be so monitored.

Sedated patients that were monitored utilizing electrical wires have been severely burned. Patients have even died because they were not phonocardiologically monitored because of the hazard of burns.

As discussed above, phonocardio electrical microphones suffer from severe pink noise rendering such devices useless below approximately 25 Hz. It is believed that most of the significant body sounds occur below 25 Hz. Utilization of the prior art sensors renders this spectral region unavailable to physicians and medical researchers. The lack of an adequate low frequency sensor has prevented medical research into low frequency spectral analysis.

Thus, it is appreciated that in MRI systems, non-metallic sensors are preferred although heretofore unavailable. Additionally, non-invasive sensors are always preferred over invasive sensors for equivalent information for the shock and burn hazard reduction that such sensors provide.

SUMMARY OF THE INVENTION

The above disadvantages of the prior art are obviated by positioning a fiber optic coupler sensor proximate an appropriate body location to detect cardiovascular audio and sub-audio sounds. The fiber optic coupler includes a plurality of input optical fibers each having a core, the cores of the optical fibers being merged and fused in a waist region to form a common optical core wherefrom a plurality of output optical fibers emerge. The fiber optic coupler distributes light energy incident to one of the input optical fibers between the plurality of output optical fibers. The common optical core is encapsulated in an encapsulant having a refractive index that is variable with stress applied thereto such that the incident light energy is distributed between the plurality of output optical fibers as a function of the stress applied to the encapsulant. Stress is induced in the encapsulant by the cardiovascular sounds to be detected. In one embodiment of the sensor, the encapsulant is formed with a relatively narrow region to increase sensitivity.

The fiber optic sensor is fabricated entirely of dielectric materials thus eliminating all shock hazards. Since pink noise does not occur in fiber optic coupler sensors, pink noise does not propagate through the detectors and amplifiers of the system thereby providing detection without one-over-frequency noise in the subhertz to 40 Hz region. The sensor is non-invasive and sensitive to cardiovascular sounds from steady state to beyond 10 KHz. The fiber optic coupler sensor is satisfactorily operative in the acoustically noisy environment and the high intensity and high frequency magnetic fields of magnetic resonance imaging machines. The absence of metallic parts eliminates all shock and burn hazards from radio frequency induced currents and heating. Detection and identification of heart sound $S_1$ through $S_4$ are achieved through clothing and without special coupling gels. Electrical shock hazards, electrical interference problems, use of special quiet rooms and danger from induced radio frequency currents common to MRI systems are eliminated. The sensor is mechanically rugged and inexpensive to manufacture.

DESCRIPTION OF THE PREFERRED EMBODIMENTS

Figure 1:
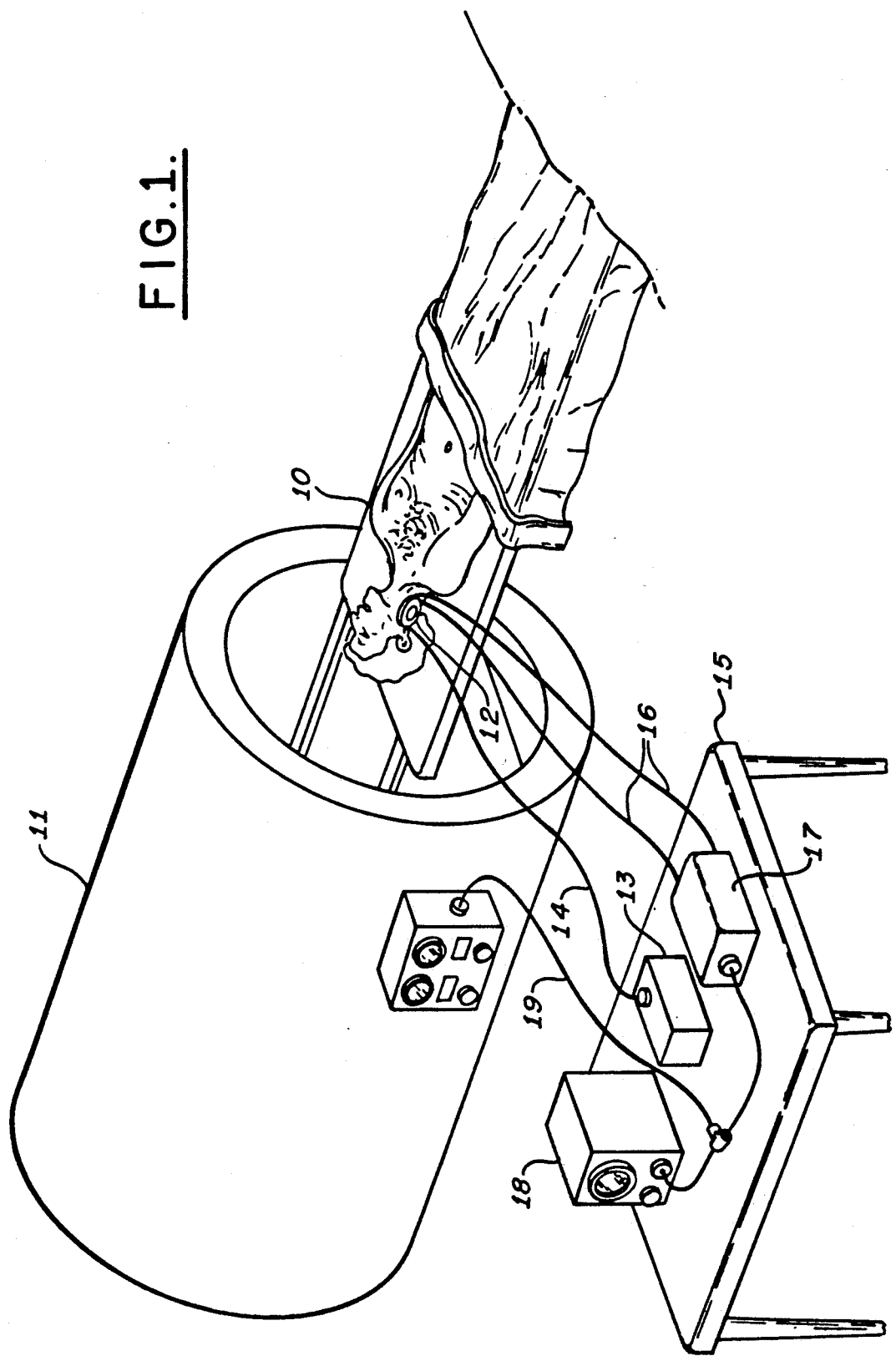
FIG. 1 is a schematic view of an MRI facility utilizing the fiber optic coupler phonocardio sensor of the present invention to detect the pulse of the patient.

Referring to FIG. 1, an MRI facility is schematically illustrated. A patient on an examination table 10 is disposed relative to an MRI system 11 for taking MRI images of the patient. In accordance with the present invention, an all dielectric fiber optic coupler phonocardio and pulse sensor 12 is disposed adjacent the patient for detecting the pulse thereof. The sensor 12 is illustrated adjacent the carotid artery in the patient's neck for performing the detection function. It is appreciated that the sensor 12 can be positioned at any other appropriate location on the patient's body. An appropriate light source 13, such as a pigtailed light emitting diode (LED) or laser is coupled to the sensor 12 by an optical fiber 14. The optical fiber 14 forms the input port of the sensor 12. The light source 13 is on an auxiliary stand 15 located a distance from the table 10. Optical fibers 16 form the output ports of the sensor 12 and are coupled to electronic detection circuitry 17 on the table 15. The electronic detection circuitry 17 provides electrical signals corresponding to the acoustic signals detected by the sensor 12 in a manner to be explained. The electrical output of the circuitry 17 is coupled to an oscilloscope 18 for visual observation. The electrical output of the circuitry 17 is also coupled via a line 19 to the MRI system 11 to provide gated imaging.

In such MRI systems, generally the purpose of the sensor 12 is not primarily to view the pulse but to gate the image of the MRI system. The sensor 12 is utilized to time or synchronize the MRI system so that images of a desired area are obtained at "quiet" intervals when the pulse pressure wave is not travelling through the area of interest. The pulse pressure wave results in momentary swelling causing spurious effects or artifacts which tend to blur the image thereby resulting in a loss of resolution.

It is appreciated that all of the metallic and electrical components of the system are disposed a distance from the patient completely eliminating shock and burn hazards. All of the components 12, 14 and 16 are of dielectric material. It is appreciated that the fibers 14 and 16 may be many kilometers in length without signal transmission problems.

Figure 2:
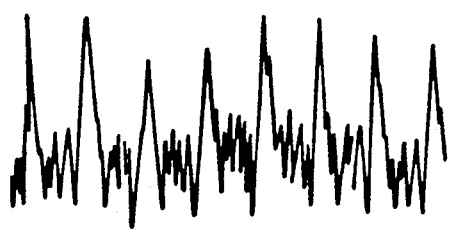
FIG. 2 is an acoustic record of a wrist pulse obtained by a coupler sensor disposed on the wrist.
Figure 3:
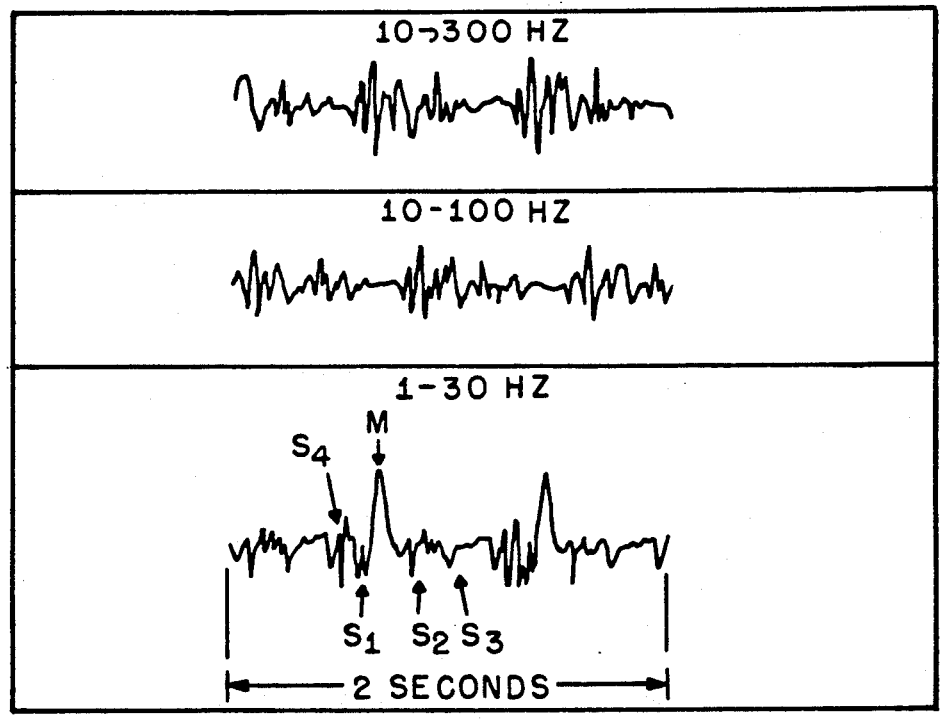
FIG. 3 comprised of traces A, B and C illustrate heart sounds detected with a coupler sensor disposed on the patient's chest with the sounds sensed through the patient's clothing.
Figure 4:
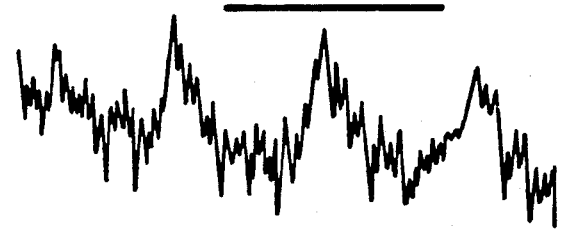
FIG. 4 is a spectral analysis of a wrist pulse obtained with the sensor in accordance with the present invention and taken with a spectrum analyzer.

Referring to FIGS. 2, 3 and 4, FIG. 2 illustrates an acoustic record of a wrist pulse obtained, in accordance with the invention, by a coupler sensor merely placed on top of the wrist. It is appreciated that electrical leads are not required to be located anywhere near the patient. FIG. 4 illustrates a spectral analysis of the wrist pulse of FIG. 2. A frequency spectrum from 0 to 5 Hz is illustrated. The spectrum was obtained over a 5 minute period with a conventional spectrum analyzer having a bandwidth of 72.6 mHz. FIG. 3 illustrates heart sounds obtained, in accordance with the invention, with a fiber optic coupler sensor. The sensor was positioned on the patient's chest and the recorded sounds were sensed through the patient's undershirt and dress shirt. $S_1$ through $S_4$ refer to the first through fourth heart sounds, respectively. The three traces 3A-3C illustrate how frequency filtering reveals different information. Waveform 3A illustrates the heart sounds in the frequency range of 10–300 Hz. Waveform 3B illustrates the heart sounds in the frequency range of 10–100 Hz and resembles a conventional phonocardiogram. Waveform 3C illustrates heart sounds in the frequency range of 1–30 Hz and illustrates the identification of heart sounds as well as a very low frequency chest response probably related to systole. Specifically, the peak M is probably due to a very low frequency chest movement during systole.

Figure 5:
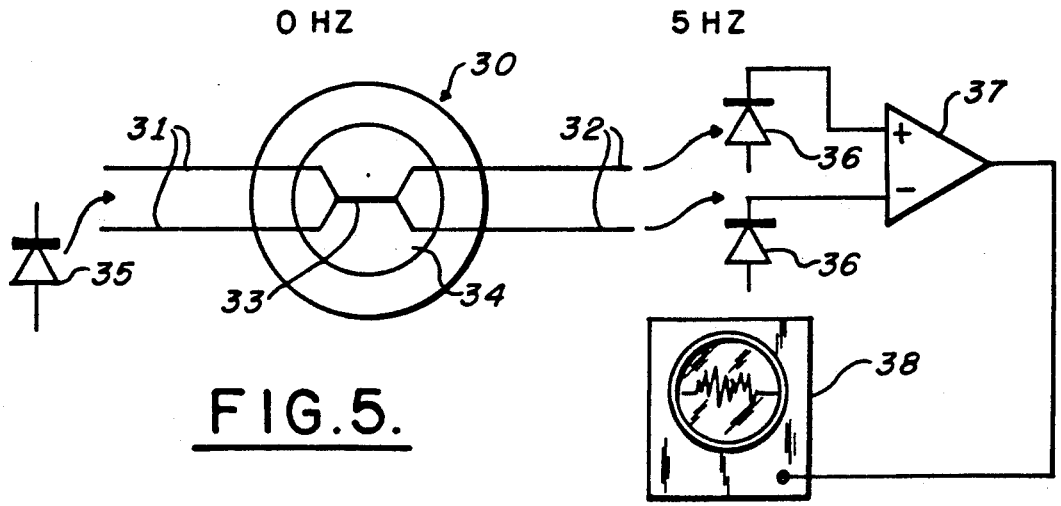
FIG. 5 is a schematic diagram illustrating the optical and electrical arrangement of the fiber optic coupler sensor.

Generally, the phonocardio sensor utilized in the present invention is of the type disclosed in U.S. Pat. No. 4,634,858, issued Jan. 6, 1987, entitled "Variable Coupler Fiber Optic Sensor" and assigned to the assignee of the present application. Said U.S. Pat. No. 4,634,858 is incorporated herein in its entirety. Referring to FIG. 5, the optical and electrical arrangement of the fiber optic coupler sensor utilized in the present invention is illustrated. Fiber optic couplers are $M \times N$ port devices which couple light from one of the M input ports to all of the N output ports. Generally, single mode couplers are $2 \times 2$ devices constructed from single mode fibers which operate over the ordinary fiber wavelengths of 633, 850, 1300, and 1550 NM.

The phonocardio sensor generally comprises a $2 \times 2$ fused tapered biconical coupler surrounded by a rubber-like medium such as silicon rubber as described in said U.S. Pat. No. 4,634,858. The preferred method of fusing the fibers is described in U.S. patent application Ser. No. 240,986, filed Sept. 6, 1988, entitled "Fiber Optic Fabrication Furnace", by D. W. Gerdt now U.S. Pat. No. 4,879,454 issued Nov. 7, 1989. Further details are disclosed in U.S. patent application Ser. No. 376,342, filed July 6, 1989, entitled "Variable Coupler Fiber Optic Sensor Hydrophone" by D. W. Gerdt. Said U.S. Ser. No. 240,986 and said U.S. Ser. No. 376,342 are assigned to the assignee of the present application and are incorporated herein in their entirety.

FIG. 5 schematically illustrates a variable coupler fiber optic phonocardio sensor 30 having input fibers 31 and output fibers 32. The sensor 30 includes a coupling joint or waist region 33 encapsulated in an encapsulant 34. The encapsulant 34 is preferably a room temperature vulcanizing (RTV) silicon rubber such as General Electric RTV-12. Light is launched into one of the input fibers 31 by a suitable light source such as a pigtailed fiber optic LED 35. Alternatively, a suitable pigtailed laser may be utilized as the light source. The light is guided by the input fiber to the coupler joint 33 where it is divided into the two output fibers 32. Preferably, the sensor 30 is constructed such that the light divides into approximately equal portions under quiescent conditions. The optical power ratio is then approximately one-to-one. The light guided into the output fibers 32 impinge upon photodetectors 36, respectively, which are preferably implemented by photodiodes. The ratio of optical power division is linearly related to the stress field at the coupling joint 33. Thus, stress in the region of the encapsulated coupler joint 33 results in a ratio change in the optical output of the fibers 32. This change in ratio is measured by the photodetectors 36 by converting the optical ratio change to a ratio change in voltage. The voltage outputs from the photodetectors 36 are differentially amplified at the inverting and non-inverting inputs of a differential amplifier 37. The output of the differential amplifier 37 conveniently provides an input to an oscilloscope 38. The output ratio of the coupler sensor 30 is extremely sensitive to strain induced in the encapsulant 34 near the coupler joint 33 by the phonocardio audible and infra-sounds to be detected.

Figure 6A:
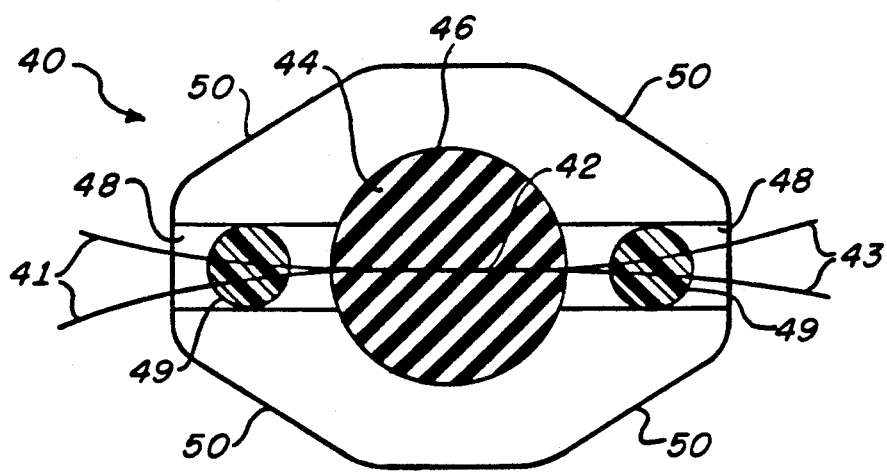
FIGS. 6a and 6b are top and side views, respectively, of the phonocardio and pulse sensor utilized with the method of the present invention illustrating construction details thereof.
Figure 6B:
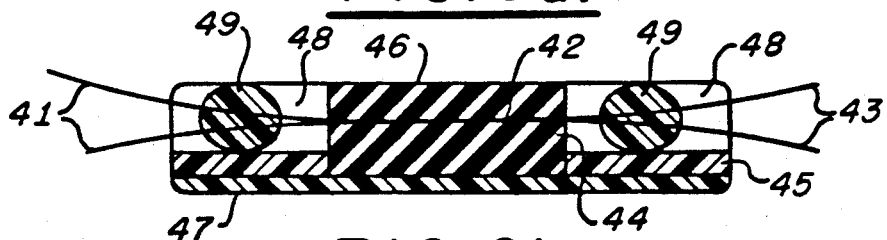

Referring to FIGS. 6a and 6b, wherein further details of the sensor utilized in accordance with the present invention are illustrated. A phonocardio sensor 40 comprising all non-electrically conducting components was utilized as a heart/pulse infra-sound and audible sound sensor. The sensor was utilized in the acoustically noisy environment of a magnetic resonance imaging system. The sensor 40 is comprised of an input optical fiber 41, a coupling, beam splitting or fusion joint 42 and output optical fibers 43. The joint 42 is encapsulated in a stress sensitive encapsulant 44 such as fast set two part GE RTV-12. The coupler 40 includes a non-metallic structural support member or body 45 preferably comprised of a plastic such as Plexiglas plastic. The plastic member 45 includes a large round hole 46 bored through the member 45 and centered thereon. A thin film 47 of polyvinyl chloride (PVC) approximately 5 micrometers thick, is stretched across the bottom of the member 45. The PVC film 47 was glued onto the plastic body 45 with quickset epoxy which was then allowed to cure. Next, the plastic body 45 with a somewhat wrinkled PVC film 47 was placed into an oven at 50° C. for five minutes. This heating process stretched the PVC film 47 tight like a drumhead. Alternatively, a heat gun may be utilized instead of the oven. Care, however, must be exercised not to tear the PVC film 47 when rapidly stretching it with a heat gun. It is appreciated, therefore, that the large hole 46 in the plastic member 45 now has a uniform bottom defined by the tight PVC film 47.

Two grooves or slots 48 are milled into the plastic member 45 and the coupler fiber elements 41, 42 and 43 are tautly fastened into the slots 48 and the hole 46 by a suitable securing means 49. Preferably, a fast cure epoxy or other rigid glue or cement is utilized. The joint 42 is surrounded by the RTV encapsulant 44. The grooves 48 function to permit the coupling joint 42 to be enclosed approximately in the center of the RTV 44. The epoxy securant 49 maintains the joint 42 tight while the RTV 44 is poured into the well formed by the hole 46 and the PVC film 47. The RTV encapsulant 44 is permitted to cure and the sensor is then ready for use.

It is appreciated that the purpose of the PVC film 47 is to form a mold surface for the RTV 44 and is not designed to affect the operation of the sensor 40. The film 47, however, could be utilized to provide sensor characteristics which could not be otherwise obtained. For example, the film 47 could be utilized to provide additional stiffness.

The plastic member 45 is provided with rounded corners 50 to facilitate access to regions of the body. For example, the sensor 40 appears to provide best performance when resting flat on the body. To obtain sound spectra emanating from the carotid artery, the sensor 40 is preferably disposed on the neck of the patient. The sensor 40 is approximately 3" in diameter and approximately ⅛" thick.

Figure 7A:
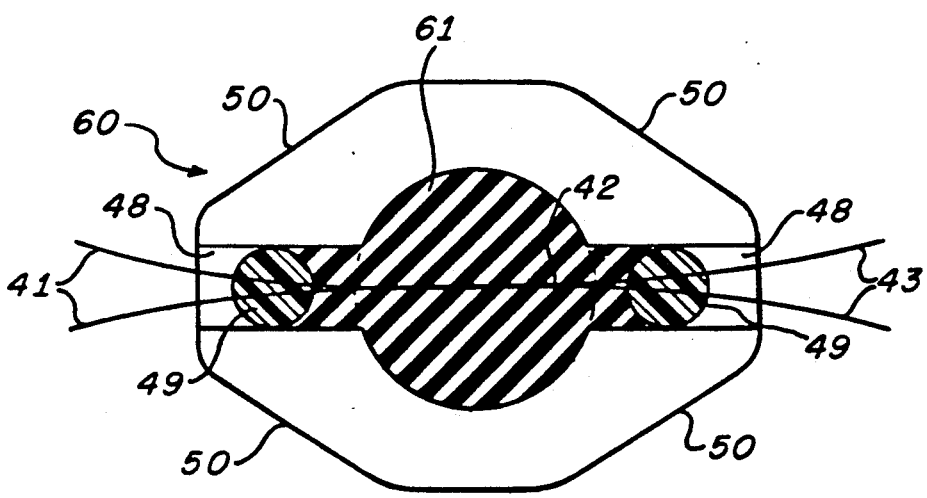
FIGS. 7a and 7b are top and side views, respectively, of an alternative construction of the sensor utilized in the method of the present invention.
Figure 7B:
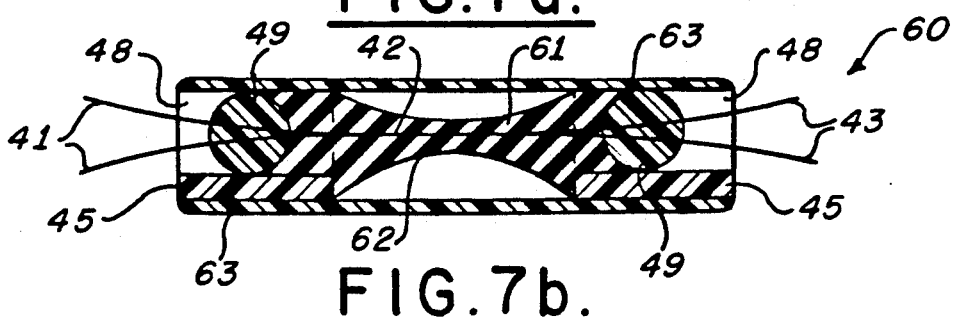

Since the PVC support film 47 is not necessary for the operation of the sensor 40, other geometries for the RTV membrane 44 are contemplated. Referring to FIGS. 7a and 7b, in which like reference numerals indicate like elements with respect to FIGS. 6a and 6b, an alternative embodiment of the sensor with a doubly concave RTV membrane is illustrated. A sensor 60 includes an RTV membrane 61 with concave contours 62. The sensor 60 also includes non-metallic protective plates 63. The concave surfaces 62 are molded into the RTV membrane 61 by wax forms which are later removed by heat or chemicals. The sensor 60 thus includes a very thin and very sensitive RTV membrane 61. The membrane 61 responds inertially as described in said U.S. Ser. No. 376,342 and is protected from being punctured by the protective plates 63. The dimensions of the sensor 60 are approximately the same as the sensor 40 of FIGS. 6a and 6b.

Figure 8A:
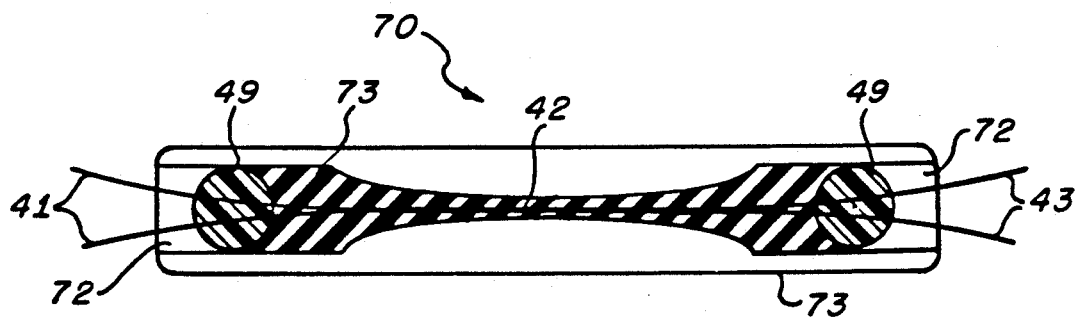
FIGS. 8a and 8b are top and side views, respectively, of a linear catheter configuration of the phonocardio and pulse sensor utilized in the method of the present invention.
Figure 8B:
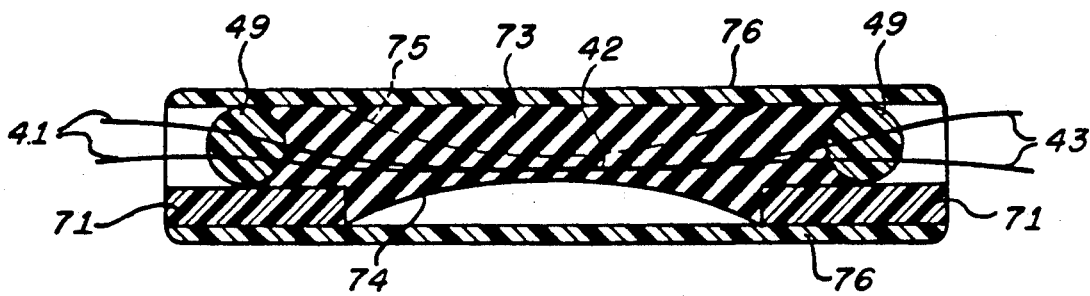

The variable coupler fiber optic sensor of said U.S. Pat. No. 4,634,858 has been constructed as a tubular sensor and has demonstrated extreme sensitivity. Therefore, a linear phonocardio/pulse sensor is contemplated. Referring to FIGS. 8a and 8b in which like reference numerals indicate like elements with respect to FIGS. 6a and 6b, a linear pulse/phonocardio sensor embodied as a catheter 70 is illustrated. In a manner similar to that described above, the sensor 70 includes a non-metallic body 71 with slots 72 milled therein. The input fiber 41, output fibers 43 and the beam splitting joint 42 are anchored in the slots 72 by the epoxy beads 49. The fibers are anchored to a structure comprising the body 71 with wax or polymeric film forms to form concave, convex or flat sections as desired. Although wax or polymeric film forms are preferred, other molding structures and processes may be utilized. As described above, RTV fills a cavity in the structure encapsulating the joint 42 and forming a sensitive membrane 73 including concave, convex or flat surfaces as desired. One side of the membrane 73 may include a concave surface 74. The other side of the membrane 73 may either be concave or flat as indicated by the dashed line 75. The sensor 70 includes protective top and bottom plates 76. The sensor 70 may be sufficiently thin to function as a catheter.

Figure 9A:
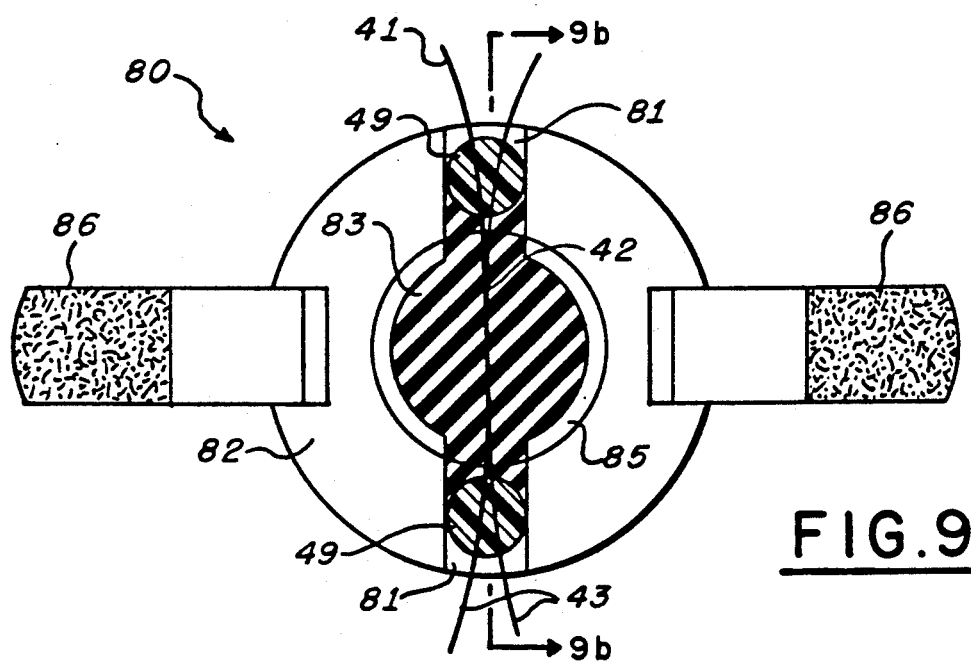
FIGS. 9a and 9b are top and side views, respectively, of a strap-on phonocardio and pulse sensor for wrist, heart and neck detection in accordance with the method of the present invention.
Figure 9B:
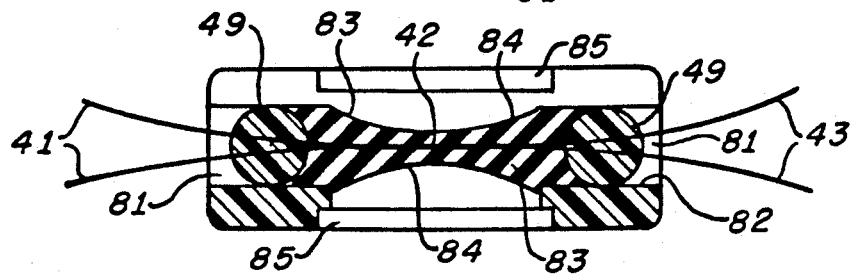

Referring to FIGS. 9a and 9b in which like reference numerals indicate like elements with respect to FIGS. 6a and 6b, a strap-on sensor 80 illustrates a mechanism for attaching the sensor to the wrist. When so utilized, the sensor 80 provides continuous monitoring of the pulse without invasive procedures. In a manner similar to that described above, the elements 41, 42 and 43 are anchored by epoxy beads 49 into milled slots 81 in a non-metallic body 82. As described above, RTV-12 elastomer is utilized to form a sensitive membrane 83. The membrane 83 may be formed with curved surfaces 84 in a manner similar to that described above. The sensor 80 includes round protective plates 85. A strap 86, such as a velcro strap, is utilized to fasten the sensor 80 to the wrist. The sensor 80 is approximately 2" in diameter and approximately ¼ of an inch thick.

It is appreciated from FIGS. 7–9 that the curved surfaces formed in the sensitive membrane significantly increases the sensitivity of the devices. It is believed that the coupler sensors as described herein can be constructed having significantly more sensitivity than electrical equivalents based on piezo effects, strain gauges and the like where low frequency response is desired. It is appreciated from the foregoing that the fiber optic sensors and optical leads utilized in the present invention are immune to electric or magnetic interference. All of the advantages of fiber optic sensors are preserved in the coupler sensor as utilized in the present invention. Coupler sensors are sensitive from DC to over 10 KHz and do not exhibit any one-over-frequency type noise. The manufacture of coupler sensors requires only simple and relatively inexpensive methods and materials. Inexpensive lasers conventionally utilized with laser discs are appropriate as light sources for the present invention once the laser is pigtailed. Immunity from electrical interference of the sensor utilized in the present invention is particularly desirable in situations encountered by emergency medical technicians. Motors, engines and power lines can render conventional EKG machines useless. Because of the great sensitivity of the above-described sensor, a weak pulse can be sensed in torn limbs which are in danger of circulation loss. Since the sensor does not have any one-over-frequency noise, there are numerous applications of the sensor for low frequency acoustic detection. The spectral analysis of body infra-sound should reveal patterns such as clogging of arteries, the mechanical condition of heart valves and general circulatory condition. This type of data could reveal higher frequency components of infra-sound due to turbulence caused by arterial constriction.

While the invention has been described in its preferred embodiments, it is to be understood that the words which have been used are words of description rather than limitation and that changes may be made within the purview of the appended claims without departing from the true scope and spirit of the invention in its broader aspects.

I claim:

1. A fiber optic coupler cardiovascular sound sensor constructed of only dielectric material for use in a non-evasive method of monitoring cardiovascular sounds, including sub-audible sound, without danger of burn or electrical shock hazard to a patient or invading the interior of said patient's body, said sensor comprising
   a plurality of input optical fibers each having a core, said cores of said optical fibers being merged and fused in a waist region to form a common optical core wherefrom a plurality of output optical fibers emerge, said fiber optic coupler sensor distributing light energy incident to one of said input optical fibers between said plurality of output optical fibers,
   a membrane encapsulating said waist region and having a refractive index variable with stress applied thereto such that said incident light energy is distributed between said plurality of output optical fibers as a function of said stress applied, a support member with a cavity and an aperture therein, said aperture extending through said support member to said cavity, said waist region encapsulated in said membrane disposed in said cavity such that said stress applied is to responsive to cardiovascular sounds coupled to said cavity through said support member, said membrane including at least one curved surface so that said membrane has a non-uniform thickness with a thinnest section, said waist region being encapsulated in said membrane so that said waist region extends through said thinnest section, thereby enhancing the sensitivity thereof to said cardiovascular sounds;
   a taut film secured across an opening of said aperture, and
   means for converting said distributed light energy emerging from said output optical fibers into corresponding electrical signals, thereby monitoring said cardiovascular sounds, including said sub-audible sound, without danger of burn or electrical shock hazard to said patient.

2. The sensor of claim 1 wherein said taut film is plastic film and, said encapsulating material is in intimate contact with said plastic film.

3. The sensor of claim 2 wherein said plastic film comprises polyvinyl chloride.

4. The sensor of claim 1 wherein said encapsulating material comprises silicon rubber.

5. The sensor of claim 1 wherein said encapsulating material comprises RTV-12 silicon rubber.

6. The sensor of claim 1 wherein said encapsulating material comprises a low index optical epoxy.

7. The sensor of claim 1 wherein said encapsulating material comprises a low index polymer.

8. The sensor of claim 1 wherein said encapsulating material comprises a low index resin.

9. The sensor of claim 1 wherein said thinnest section of said membrane is at the center thereof.

10. A fiber optic coupler cardiovascular sound sensor constructed of only dielectric material for use in a non-evasive method of monitoring cardiovascular sounds, including sub-audible sound, without danger of burn or electrical shock hazard to a patient or invading the interior of said patient's body, said sensor comprising
   a plurality of input optical fibers each having a core, said cores of said optical fibers being merged and fused in a waist region to form a common optical core wherefrom a plurality of output optical fibers emerge, said fiber optic coupler sensor distributing light energy incident to one of said input optical fibers between said plurality of output optical fibers,
   a membrane encapsulating said waist region and having a refractive index variable with stress applied thereto such that said incident light energy is distributed between said plurality of output optical fibers as a function of said stress applied,
   a support member with a cavity and an aperture therein, said aperture extending through said support member to said cavity, said waist region encapsulated in said membrane disposed in said cavity such that said stress applied is to responsive to cardiovascular sounds coupled to said cavity through said support member, said membrane including at least one curved surface so that said membrane has a non-uniform thickness with a thinnest section, said waist region being encapsulated in said membrane so that said waist region extends through said thinnest section, thereby enhancing the sensitivity thereof to said cardiovascular sounds;

means for converting said distributed light energy emerging from said output optical fibers into corresponding electrical signals, thereby monitoring said cardiovascular sounds, including said sub-audible sound, without danger of burn or electrical shock hazard to said patient.

* * * * *